United States Patent [19]

Staempfli

[11] 4,391,272
[45] Jul. 5, 1983

[54] DISPOSABLE SYRINGE

[75] Inventor: Jackie Staempfli, Paris, France

[73] Assignee: Tulcea, S.A., Vaduz, Liechtenstein

[21] Appl. No.: 19,251

[22] Filed: Mar. 9, 1979

[30] Foreign Application Priority Data

Mar. 10, 1978 [CH] Switzerland ............ 2624/78

[51] Int. Cl.³ ................................. A61M 5/00
[52] U.S. Cl. ...................................... 604/110
[58] Field of Search ......... 128/218 P, 218 PA, 218 C, 128/218 R, 215, 216, 219, 234

[56] References Cited

U.S. PATENT DOCUMENTS

| | | | |
|---|---|---|---|
| 2,375,711 | 5/1945 | Vondrak | 128/218 C |
| 2,607,343 | 8/1952 | Sarver | 128/218 C |
| 3,045,674 | 7/1962 | Goldberg | 128/218 P |
| 3,946,732 | 3/1976 | Hurscham | 128/218 M |
| 3,951,146 | 4/1976 | Arias | 128/218 R |
| 4,030,498 | 6/1977 | Tompkins | 128/218 P |
| 4,233,975 | 11/1980 | Yerman | 128/218 P |

FOREIGN PATENT DOCUMENTS

| | | | |
|---|---|---|---|
| 112893 | 1/1969 | Denmark | 128/218 P |
| 2298340 | 8/1976 | France | 128/218 P |

Primary Examiner—John D. Yasko
Attorney, Agent, or Firm—Cushman, Darby & Cushman

[57] ABSTRACT

The invention relates to a disposable syringe which is not able to be used more than once for carrying out an injection.

To this end, the syringe comprises means which permit the rearward return of at least a part of the piston body to be prevented when the said body occupies a position close to its position of maximum insertion in the cylinder. These means can, for example, be formed by a circular groove, in which can be engaged a peripheral rim of a resilient member integral with the body of the piston, thus causing the blocking of the said body.

Applications are particularly in human and veterinary medicines.

10 Claims, 11 Drawing Figures

DISPOSABLE SYRINGE

FIELD OF THE INVENTION

The present invention relates to a disposable syringe, i.e., a syringe which can only be used once for making an injection.

The need to have available a syringe which cannot be used again is very keenly felt at the present time, particularly because a large number of injections of medicinal or other substances are carried out by the patients themselves, that is to say, without the assistance of members of the medical service, under conditions which do not permit an effective sterilisation of the syringe before it is used.

BACKGROUND OF THE INVENTION AND DESCRIPTION OF THE PRIOR ART

Syringes intended for being used only for a single injection are already known. For example, French Patent Application No. 76 12 199 describes a combined ampoule and syringe, in which the piston carries, at its end placed inside the cylinder of the syringe, a joint which is separable from the piston, which is designed to remain in its final position at the bottom of the cylinder when the injection has been carried out. A retraction of the rod causes a separation between the rod and the joint of the piston. However, this syringe does not permit a liquid to be drawn in from an ampoule. On the other hand, in the construction as proposed, it is an easy matter to remove the joint or packing of the cylinder from the syringe by other means and to use the syringe again after having refilled it. German Patent Application No. 17 66 748 proposes a syringe of which the rod is provided with a locking device for preventing the return of the piston from a position of maximum insertion. Nevertheless, this arrangement, situated outside the cylinder, can be easily detached or made inoperative, so that this syringe does not give any guarantee for it not to be used again.

An effectively disposable syringe is described in French Patent Application No. 75 15 412. It comprises means associated with that part of the piston which is disposed inside the cylinder and permitting a single intake and ejection movement of the piston.

Now it is frequently necessary to effect the injection of a mixture of several different liquid substances, which mixture cannot be prepared in advance, but only at the moment of injection. This involves the necessity of having available a syringe which is capable of being filled in several steps, that is to say, a syringe of which the piston can carry out an indefinite number of reciprocatory movements during the filling of the cylinder before the operation of injection.

OBJECTS OF THE INVENTION

One object of the invention is to provide a syringe which offers the guarantee that it cannot be used for more than a single injection.

A further object of the invention is to provide a syringe which permits a filling in several steps, if necessary.

A further object of the invention is to provide a syringe which is of simple design and can be manufactured in large numbers at a minimum cost price.

These and other objects and advantages of the invention will appear from the following description and claims.

SUMMARY OF THE INVENTION

The disposable syringe according to the invention, comprises a cylinder of which one end is provided with a nozzle permitting the fixation of a needle, an intake and delivery piston comprising a body arranged so as to form a tight movable partition capable of sliding inside the cylinder, a rod fast with the body of the piston and permitting the latter to be displaced with a sliding movement in the cylinder, and means preventing the rearward return of at least a part of the body of the piston when the said body occupies a position close to its position of maximum insertion into the cylinder.

The invention will be best understood by reference to the description which is to follow and by reference to the accompanying drawings, in which are illustrated, diagrammatically and by way of example, for particular constructional forms of the syringe according the the invention.

DESCRIPTION OF THE PREFERRED EMBODIMENTS

Figure 1A:
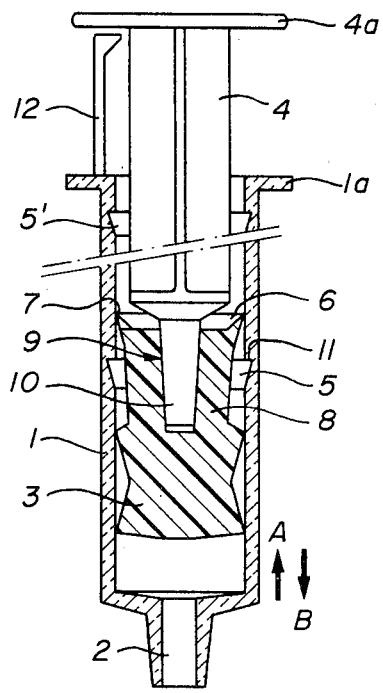
FIGS. 1a, 1b, and 1c are general views, in longitudinal axial section, of a first embodiment of the syringe according to the invention, respectively showing the position occupied by the piston in the cylinder before the syringe is used, after a first use for effecting an injection and, soon afterwards, the start of an attempt to reuse the syringe.
Figure 1B:
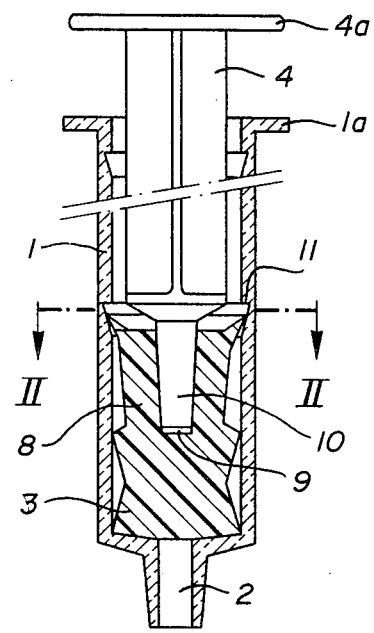
Figure 1C:
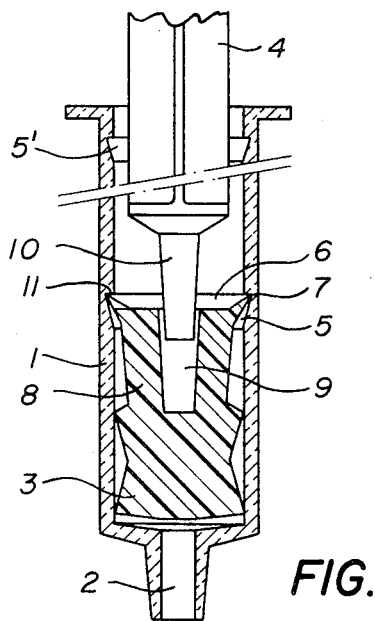

The syringe which is shown in FIGS. 1a, 1b, and 1c comprises a cylinder 1, one end of which is formed with a nozzle 2 permitting an injection needle to be fixed thereon and an intake and delivery piston which consists of a body 3 forming a tight movable partition which is capable of sliding, while maintaining the tightness, along the inside wall of the cylinder 1, and a piston rod 4. The cylinder 1, the body 3 and the piston rod 4 may for example be formed by synthetic resin.

That end of the cylinder 1 which is opposite the nozzle 2 carries a collar in the form of a flat ring 1a as means for gripping and actuating the syringe, the end of the piston rod 4 outside the cylinder 1 being provided with a disc 4a forming an integral part of the rod 4, thus also serving as gripping and actuating means.

That end of the piston rod 4 which is disposed inside the cylinder 1 is provided with a frustoconical fixing neck 10 which is engaged as a force fit in a frustoconical axial recess 9 formed in an assembly member 8 which is integral with the body 3 of the piston. The recess 9 and the neck 10 have the same conicity, which makes it possible, when the neck 10 is engaged with a suitable force in the recess or cavity 9, to obtain the required solidarity between the rod 4 and the piston body 3 for permitting the displacement of this latter in the cylinder 1, by an action applied to the rod 4. In the example as shown in FIGS. 1a, 1b, and 1c, the assembly member 8 is in one piece with the piston body 3. This piece is preferably made of a material which has a certain elasticity, for example, of a synthetic plastic material, in order to ensure a good tightness by sliding action between the piston body 3 and the inside wall of the cylinder 1. However, as a modification, the body 3 of the piston could be made of a relatively hard material, in which case only the separate member 8 fast with the part of the body 3 is then formed of an elastic material.

Figure 2:
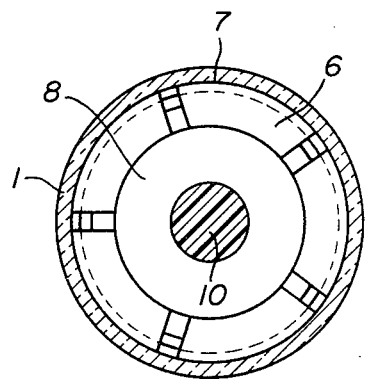
FIG. 2 is a sectional view along a horizontal plane represented by the line II—II in FIG. 1b.

The free end of the assembly member 8 is flared and forms a resilient member 6 of collar-like form which has a peripheral rim 7. As will be seen from FIG. 2, the collar 6 is divided into five sectors which are separated by notches. Because of the elasticity of the member 6, the rim 7 has a tendency to bear against the inside wall of the cylinder 1, this effect being facilitated by the collar being divided into sectors. It is obvious that there could be any desired number of the said sectors and the division of the member 6 into sectors is in any case not essential for obtaining the tendency of the rim 7 to be applied to the inside wall of the cylinder 1.

The inside wall of the cylinder 1 is formed with a circular groove 5 perpendicular to the axis of the cylinder 1. The groove 5 has a shape which in general is approximately frustoconical, the top of the cone being directed toward the nozzle end 2. Moreover, the groove 5 has such a shape and position that if the piston body 3 is driven to its full extent into the cylinder 1, the rim 7 of the resilient member 6 is adapted to engage in the groove 5, remaining supported against the wall of the cylinder 1, this causing the increase in size of the opening of the collar 6. That edge 11 of the groove 5 which is opposite the end of the cylinder 1 carrying the nozzle 2 is sufficiently abrupt that, once the rim 7 of the member 6 is engaged in the groove 5, it becomes locked against the edge 11, if an attempt is made to pull back the piston body 3.

A groove 5' of a shape identical with that of the groove 5 is in addition provided close to the upper end of the cylinder 1. The function of this groove 5' is to make impossible, by blocking the rim 7 of the member 6, any attempt to dismantle the syringe before it is used. The presence of the groove 5' thus prevents, for example, the rim 7 of the resilient member 6 being removed before the syringe is employed, with a view to making the said syringe capable of being used again.

The syringe is, in addition, provided with a removable safety member 12, which is formed by a rod fixed at one of its ends on the ring 1a and slightly bent over towards the axis of the poston rod 4 at its other end. The rod 12 may either form an integral part of the cylinder 1 or be formed by a part separate from the latter.

The purpose of the safety member 12 is to prevent the piston being driven into the cylinder before the syringe is used, into a position such that the rim 7 of the member 6 would be engaged in the groove 5.

The syringe is thus delivered and stored, prior to being used, with the safety member 12 in position. Furthermore, it is advantageously delivered and kept in condition and in a sterile package.

The syringe which has just been described operates in the following manner:

At the moment when the syringe is used for the first time, the piston being in the position which is shown in FIG. 1a, the syringe is filled in the usual manner by first of all drawing in the liquid to be injected, by pulling the piston rearwardly in the direction indicated by the arrow A in FIG. 1a, and then, clearing the air which is in the cylinder, by driving the piston body 3 in the direction of the nozzle 2, this being in the direction indicated by the arrow B, after having reversed the position of the syringe, so that the nozzle 2 is facing upwardly.

It is seen that, because of the presence of the safety member 12, the piston is unable to reach a locking position during the filling of the syringe, even if this filling operation is carried out in several steps, each involving a reciprocatory movement of the piston in the cylinder (in the direction of the arrow A for drawing in the liquid and in the direction of the arrow B for removing the air).

It is only at the moment of making the injection that the safety member 12 is removed, by breaking off or tearing away its end which is fixed on the ring 1a, this permitting the piston to be driven as far as the bottom of the cylinder.

When the first injection operation is completed, the body 3 of the piston is completely driven into the cylinder, in the position as shown in FIG. 1b, the rim 7 of the resilient member 6 being engaged in the groove 5.

If it is then attempted once again to use the syringe, by pulling on the piston rod 4, so as to draw into the cylinder 1 a fresh dose of liquid for injection, the rim 7 of the member 6 becomes blocked against the body 11 of the groove 5, as shown in FIG. 1c, this preventing the rearward return movement of the piston body 3. If an attempt is made to free the rim 7, the conical neck of the rod 4 becomes detached from the assembly member 8, by being pulled out of the recess or cavity 9 (FIG. 1c).

It thus becomes impossible for the syringe to be used again after the latter has been first employed.

Figure 3A:
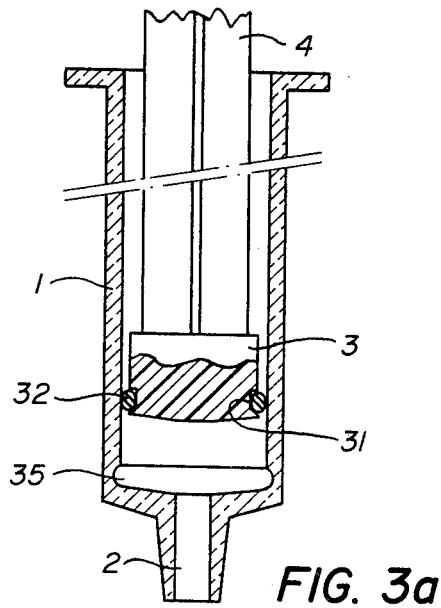
FIGS. 3a and 3b are general views in axial longitudinal section of a second embodiment of the syringe according to the invention.
Figure 3B:
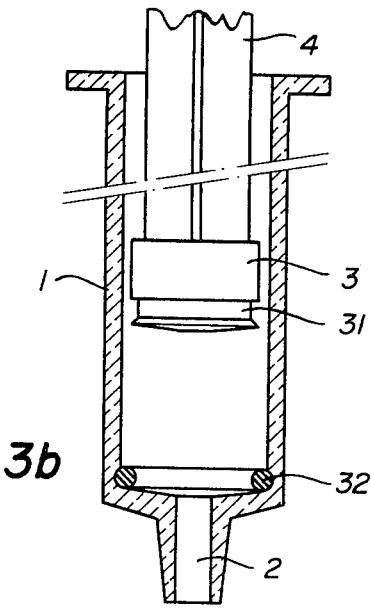

Like the syringe which has just been described, the syringe which is shown in FIGS. 3a and 3b comprises a cylinder formed with a nozzle 2, and a piston consisting of a body 3 and a rod 4.

The piston body 3 comprises a resilient sealing joint 32 which has the form of an O-ring in the absence of any force being exerted on it. When the syringe is in the operational state, the joint or packing 32 is held against the body 3 of the piston by being wedged between the inside wall of the cylinder 1 and a circular channel 31 formed in the piston body 3. In this position the packing 32 assumes a slightly flattened form in section. The inside wall of the cylinder 1 is formed with a circular groove 35 which is perpendicular to the axis of the cylinder 1. The sectional form of the groove 5 is approximately circular and its radius is sufficient to permit of accommodating the O-ring 32. The groove 35 is positioned close to that end of the cylinder which carries the nozzle 2, in a position such that when the piston body 3 is forced to the bottom end of the cylinder 1, the O-ring packing reaches a position facing the groove 35, so that it has a tendency partially to re-enter the said groove, thereby reassuming its original toric shape of circular section. In this position, the joint or packing 32 is only lightly held in the groove 31 of the piston body 3 and, if the said body is pulled rearwardly, the packing remains held in the groove 35 and becomes detached from the piston, assuming the position which is shown in FIG. 3b.

As a result, the tightness of the piston is removed and it becomes impossible once again to use the syringe, so that the latter can only be employed for making a single injection.

Before the syringe is used, the piston is placed in the position which is shown in FIG. 3a and it is prevented from being pushed in prematurely, as in the case of the syringe which is shown in FIGS. 1a, 1b, and 1c, by the safety member 12 (not shown).

Figure 4A:
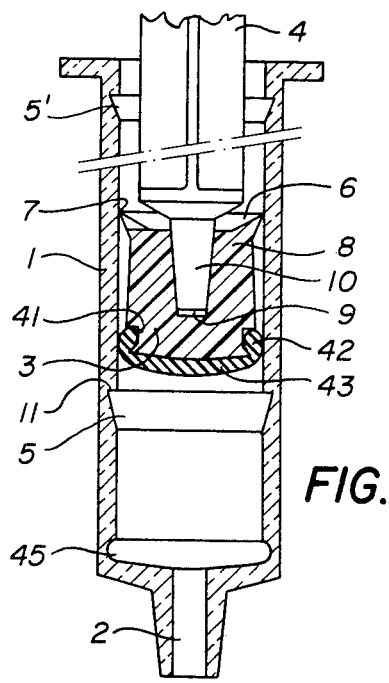
FIGS. 4a and 4b are general views in axial longitudinal section of a third embodiment of the syringe, respectively showing the position occupied by the piston on the cylinder before the syringe is used and after a first use, followed by an attempt to reuse it.
Figure 4B:
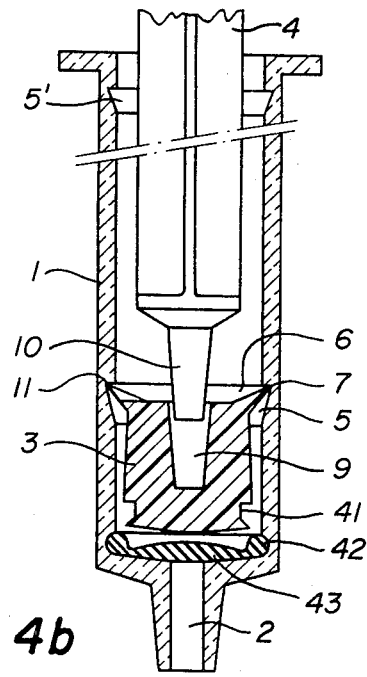

The syringe which is shown in FIGS. 4a and 4b corresponds to a constructional form which represents a combination of the two embodiments as previously described.

The syringe comprises a cylinder 1, formed with a nozzle 2, and a piston consisting of a body 3 and a rod 4. The piston rod 4 and the piston body 3 are assembled, as with the constructional form of the syringe shown in FIGS. 1a, 1b, and 1c, by a frustoconical neck 10 of the rod 4 being engaged by force into a frustoconical axial cavity 9 of corresponding conicity, formed in an assembly member 8 forming one piece with the piston body 3. The end of the assembly member 8 also forms a resilient member 6 having a rim 7 which tends to be applied to the inside wall of the cylinder 1.

When the syringe is in a position for functioning (FIG. 4a), a resilient sealing joint 43 is held fast with the piston body 3 by wedging a toroidally shaped part 42 of this joint between a peripheral groove or channel 41 formed at the lower end of the piston body 3 and the inside wall of the cylinder 1.

The inside wall of the cylinder 1 is formed with a circular groove 5 which co-operates with the resilient member 6 so as to permit the blocking of the piston body 3 in a position close to its maximum position of insertion and the possible disengagement of the piston rod 4 (FIG. 4b), as was the case in the first constructional form of the syringe as described above. The inside wall of the cylinder 1 also comprises a circular groove 45 which permits the sealing joint or packing 43 to be retained and for it to be disengaged from the piston body 3 (also seen in FIG. 4b), if another attempt is made to use the syringe after having carried out a first injection by means of the said syringe, as in the case of the second embodiment which has been described above. In addition, the inside wall 1 of the cylinder is formed with a groove 5', positioned close to the upper end of the cylinder 1, as was the case with the constructional form of the syringe as shown in FIGS. 1a, 1b, and 1c.

It is apparent that it becomes impossible for the syringe to be used again after it has been employed for making a first injection, firstly because of the definitive elimination of the tightness of the piston when the said piston is pulled backwardly from its position of maximum insertion, then because of the blocking of the piston body 3 and finally because of the detachment of the rod 4 from the piston body 3, it being possible for this blocking action and this detachment to be considered as safety measures which complement the elimination of the tightness of the piston.

The premature pressing in of the piston, before the syringe is used, is also prevented by a safety member 12 (not shown).

Figure 5A:
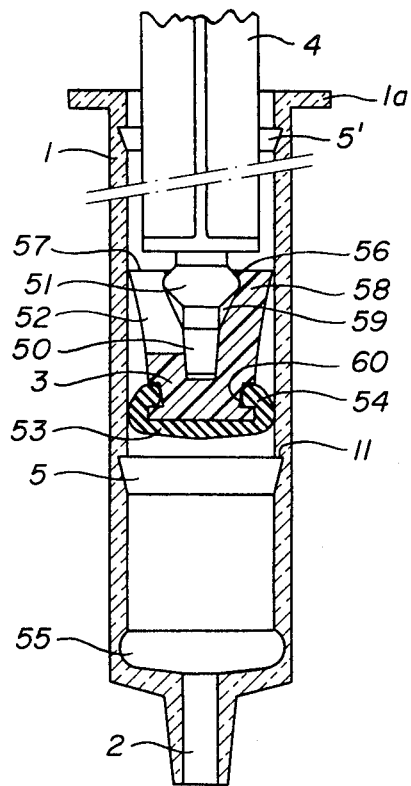
FIGS. 5a and 5b are general views in axial longitudinal section of a fourth embodiment of the syringe, respectively showing the position occupied by the piston in the cylinder, before the syringe is used, and the position which it occupies after a first use, and the start of an attempt to reuse the syringe.
Figure 5B:
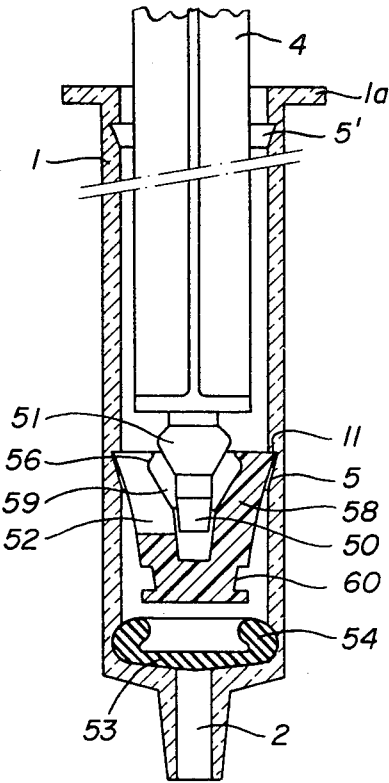

The constructional form of the syringe which is shown in FIGS. 5a and 5b is a modification of that which is shown in FIGS. 4a and 4b. As in the other constructional forms, this syringe comprises a cylinder 1 formed with a nozzle 2, and also a collar 1a, a piston rod 4, formed with a disc 4a, a piston member 3 and a safety member 12 (not shown), preventing the piston from being forced prematurely into the cylinder.

The piston body 3 comprises an assembly member 58 with the piston rod, this member 58 being formed by a resilient block of generally frustoconical form, of which the edges of the part of maximum diameter form an elastic rim 57 which tends to bear against the inside wall of the cylinder 1 and which comprises a flared axial cavity 59, having an inside latching edge 56, and at least one longitudinal notch 52, which extends through this block from its outside wall to the inside wall of the cavity 59. The end of the piston rod 4, on the side of the piston body 3, is formed with a frustoconical fixing neck 50, which is itself provided with a bulge or bulbous member 51. The shape and the dimensions of the neck 50 and those of the assembly member 58 are such that, prior to the locking of the piston body 3 in the cylinder 1, the fixing neck 50 of the piston rod 4 is retained in the assembly member 58 of the piston body. As in the constructional form which is shown in FIGS. 1a, 1b, and 1c, the inside wall of the cylinder 1 is formed with circular grooves 5 and 5' perpendicular to the axis of the cylinder 1, these grooves serving purposes similar to those of the corresponding grooves of the first constructional form of the syringe. When the resilient rim 57 of the member 58 is engaged in the groove 5, the degree of flaring of the cavity 59 of the assembly member 58 increases, this having the effect of freeing the fixing neck 50 from the engaging edge 56. The rod 4 is thus capable of being separated from the piston body 3, with greater efficiency as the rim 56 of the edges of the member 58, in being blocked against the edge 11 of the groove 5, acts in opposition of recoil of the member 58 from the position of maximum introduction of the piston into the cylinder 1.

When the syringe is in the operational state (FIG. 5a), a resilient sealing joint 53 is held fast with the piston body 3 by wedging of a part of toroidal form 54 of this joint between a peripheral groove or notch 60 formed at the lower part of the piston body 3 and the inside wall of the cylinder 1.

As well as having the circular groove 5, the inside wall 1 of the cylinder is formed with a circular groove 55, which has a shape, a position and a function similar to those of the groove 35 in the constructional form of the syringe which is shown in FIGS. 3a and 3b and of the groove 45 in the constructional form shown in FIGS. 4a and 4b.

Thus, the groove 55 retains the joint or packing 53 and disconnects it from the piston body 3, thereby pulling it from the groove 60 (FIG. 5b), if an attempt is made to use the syringe again after it has first been used.

Consequently, as is the case with the constructional form of the syringe which is shown in FIGS. 4a and 4b, the re-use of the syringe is prevented, first of all because of the elimination of the tightness of the piston, then, as safety measure, by the blocking of the piston body 3 and, finally, by the detachment of the rod 4 from the piston body 3.

Figure 6:
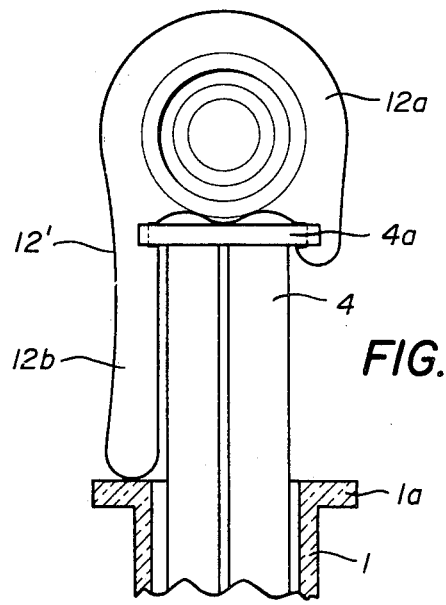
FIG. 6 is a view in elevation of the part of the piston rod outside the cylinder provided with a removable safety member, this view being designed to illustrate one particular constructional form of this last member.

The safety member 12', which is shown in FIG. 6, comprises essentially a gripping disc 12a and a blocking rod 12b. This member can be fixed detachably to the piston rod 4, and it may for example be made of plastic material. The disc 12a permits the piston rod 4 to be actuated as the time of filling the cylinder with the liquid to be injected. So as to be able to carry out the injection, once the cylinder is filled and the discharge of air is effected, it is sufficient to separate the disc 12a and the rod 12b from the piston rod 4.

The syringe according to the invention can be used in the same manner as the known syringes in all the applications of these latter, especially in connection with human and verterinary medicine.

I claim:

1. A disposable syringe comprising:
   a cylinder, one end of which cylinder is formed with a nozzle whereby a syringe needle can be fixed to the cylinder;
   an intake and delivery piston capable of sliding inside said cylinder comprising a body arranged so as to form a tight movable partition, said body having a circular groove or channel;
   a rod connected with the piston body so as to permit said body to be displaced by sliding movement in the cylinder;
   at least one resilient member provided in said piston body and having at least one peripheral rim or flange tending to be applied to the inside wall of said cylinder;
   at least one resilient sealing joint provided in said piston of which at least one peripheral part in the form of an O-ring is retained by a wedging action between the inside wall of the cylinder and said circular groove or channel of said piston body;
   at least a first circular groove, in the inside wall of said cylinder, perpendicular to the axis of the cylinder and having an edge capable of retaining the rim of the resilient member; and
   at least one second circular groove, in the inside wall of said cylinder, perpendicular to the axis of the cylinder and arranged in such a way as to receive the toroidal part of the sealing joint;
   whereby the said first groove and said second groove are so disposed as to cause, when the piston body is pulled in a rearward direction, the disconnection of the sealing joint from the piston body and the retention thereof in the second groove, and then the locking of the rim or edge of the resilient member against the edge of the first groove opposite to that end of the cylinder which has the nozzle.

2. A disposable syringe comprising:
   a cylinder, one end of which cylinder is formed with a nozzle whereby a syringe needle can be fixed to the cylinder;
   an intake and delivery piston capable of sliding within said cylinder comprising a body arranged so as to form a liquid-tight movable partition;
   a rod connected with the piston body so as to permit said body to be displaced by sliding movement in the cylinder;
   means for preventing the rearward return of at least a part of the piston body when said body occupies a position close to its position of maximum injection in the cylinder comprising at least one circular groove formed in the inside wall of the cylinder, perpendicular to the axis of said cylinder; and a resilient member on said piston body having at least one peripheral rim tending to be applied to the inside wall of said cylinder; said groove and said rim being arranged whereby, when a movement for retracting the piston from a position of maximum introduction of the piston body into the cylinder is initiated, the rim of said resilient member comes into engagement in said groove and is blocked against an edge of the latter opposite to that end of the cylinder which carries the nozzle, so as to prevent a withdrawal movement of the piston body;
   an assembly member formed by a resilient block of generally frustoconical form in said piston body, the edges of the part of said block of maximum diameter forming a resilient rim tending to be applied to the internal wall of the cylinder and the block comprising a flared axial cavity, providing an internal locking edge and at least one longitudinal notch, extending through the said block from its outside wall to the inside wall of the cavity; and
   a frustoconical fixing neck provided at the end of said piston rod, said neck having a bulbous portion, the shape and the dimensions of said neck and those of said assembly member being such that, before the locking of the piston body in the cylinder, the fixing neck of the piston rod is retained in the assembly member of the piston body, whereas, when the elastic rim of this member is engaged in the groove of the inside wall of the cylinder, the degree of flaring of the cavity of the assembly member increases so as to have the effect of freeing the fixing neck from the locking or engagement edge.

3. A disposable syringe comprising:
   a cylinder, one end of which cylinder is formed with a nozzle whereby a syringe needle can be fixed to the cylinder;
   an intake and delivery piston capable of sliding within said cylinder comprising a body arranged so as to form a liquid-tight movable partition;
   a resilient end joint or packing in said piston body comprising at least one part of toroidal form;
   a first circular groove or channel formed in the piston body, whereby a part of said toroidal form is retained by wedging action between the inside wall of the cylinder and said groove;
   a second circular groove formed in the inside wall of the cylinder perpendicular to the axis of the cylinder, of which groove the section is sufficient to receive the toroidal part of the sealing joint of the piston, thereby causing is disengagement from said first groove or channel of the piston body, said second groove being positioned close to that end of the cylinder which carries the nozzle, in such a position that when the piston body is forced to its full extent into the cylinder, the sealing joint comes opposite to said second groove when the piston body occupies a position close to its position of maximum insertion, so that it is disengaged, under the effect of its elasticity, from said first groove or channel of the piston body, as a result becoming disconnected from said piston body, and that it remains held in said second groove if a rearward pulling action is applied to the piston body;
   a rod connected with the piston body so as to permit said body to be displaced by sliding movement in the cylinder; and
   means for preventing the rearward return of at least a part of the piston body when said body occupies a position close to its position of maximum injection in the cylinder.

4. The syringe of claim 3, wherein said sealing joint forms a cover capping the face of the piston body opposite to the piston rod.

5. The syringe of claim 3, wherein said sealing joint is an O-ring.

6. A disposable syringe comprising:

a cylinder, one end of which cylinder is formed with a nozzle whereby syringe needle can be fixed to the cylinder;

an intake and delivery piston capable of sliding within said cylinder comprising a body arranged so as to form a liquid-tight movable partition;

a rod connected with the piston body so as to permit said body to be displaced by sliding movement in the cylinder;

means for preventing the rearward return of at least a part of the piston body when said body occupies a position close to its position of maximum injection in the cylinder comprising at least one groove formed in the inside wall of the cylinder; and a resilient member on said piston body having at least one peripheral rim tending to be applied to the inside wall of said cylinder; said groove and said rim being arranged whereby, when a movement for retracting the piston from a position of maximum introduction of the piston body into the cylinder is initiated, the rim of said resilient member comes into engagement in said groove and is blocked against an edge of the latter opposite to that end of the cylinder which carries the nozzle, so as to prevent a withdrawal movement of the piston body;

an assembly member formed by a resilient block in said piston body, at least one edge of said block forming a resilient rim tending to be applied to the internal wall of the cylinder and the block comprising axial cavity, providing an internal locking edge and at least one notch, extending through said block from its outside wall to the inside wall of the cavity; and a fixing neck provided at the end of said piston rod, whereby before the locking of the piston body in the cylinder, the fixing neck of the piston rod is retained in the assembly member of the piston body, whereas, when the elastic rim of this member is engaged in the groove of the inside wall of the cylinder, so as to have the fixing neck freed from the locking or engagement edge.

7. The syringe of claim 6, wherein an assembly member formed with a frustoconical axial cavity is provided in said piston body; and a frustoconical fixing neck is provided at that end of said piston rod adjacent the piston body, said neck having a conicity corresponding to that of said cavity, and said neck being engaged with a force fit in said cavity with a force sufficient to ensure the solidarity required between the piston rod and the piston body for permitting the displacement of this body, by traction applies to the rod before the locking of the piston body in the cylinder, but sufficiently small to permit the neck to be pulled out of the cavity when the rim of the resilient member is locked against the edge of the groove.

8. The syringe of claim 6, including at least one removable safety member arranged so as to prevent the piston body from being forced into a position prior to use whereby said means for preventing the rearward return of at least a part of the piston body is prevented from coming into operation.

9. In a disposable syringe having a cylinder, one end of which cylinder is formed with a nozzle;

an intake and delivery piston capable of sliding within said cylinder forming a liquid-tight movable partition; and a rod connected with the piston body so as to permit said body to be displaced by sliding movement in the cylinder, the improvement which comprises at least one circular groove formed in the inside wall of the cylinder, perpendicular to the axis of said cylinder; resilient means on said piston body which engages said groove for preventing the rearward return of at least a part of the piston body when said body occupies a position close to its position of maximum injection in the cylinder; and means connecting said rod and said piston body which is capable of ensuring between them a sufficient solidarity for permitting the piston body to be displaced rearwardly so as to cause the intake of a liquid into the cylinder through the nozzle, by traction applied to the piston rod, when the piston body has not been placed in its end position as regards the insertion travel, said connecting means being however capable of permitting the disengagement of the piston body after the resilient member has engaged in the groove, whereby a tractive force exerted on the piston rod, after the rim of the resilient means has been blocked against the edge of the groove, has the effect of disconnecting the rod from the piston body.

10. A single-use syringe comprising in combination: a tubular element having a plunger reciprocatably mounted in a first open end to tubular space of the tubular element and having an injection needle operably mounted on a remaining opposite end of the tubular element, a hollow portion of needle-through-space being in flow communication with tubular space of the tubular element, the improvement being at least one of (a) an interior wall of the tubular element and (b) a circumscribing lengthwise-wall of the plunger, including a male member and the other thereof including a female member preventing retraction of a terminal end-portion of the plunger when the plunger is inserted within the tubular space sufficiently for the male member to become aligned with the female member, at least one of the male member and the female member being movable such that the male member is lockable into the female member, whereby a non-reusable syringe results preventing refilling or reinjection in use thereof, said plunger including a terminal end that blocks further outflow of syringe contents when said male member is mated with said female member, and said plunger including a separable proximal end jointly movably axially to and fro prior to and until said male member is mated with said female member, said proximal end being detachable from said terminal end when withdrawal pressure is applied to said proximal end after the male member is mated with the female member whereby the terminal end continues to block outflow of syringe contents when an effort is made to withdraw the plunger.

* * * * *